United States Patent [19]

Becker et al.

[11] Patent Number: 4,663,303
[45] Date of Patent: May 5, 1987

[54] PROCESS FOR PREPARING SILVER CATALYSTS

[75] Inventors: Mitchell Becker, Teaneck; Kindtoken H. Liu, Maywood, both of N.J.

[73] Assignee: The Halcon SD Group, Inc., Little Ferry, N.J.

[21] Appl. No.: 832,099

[22] Filed: Feb. 24, 1986

[51] Int. Cl.$^4$ ............................................. B01J 23/50
[52] U.S. Cl. ................................. 502/170; 502/243; 502/347; 502/348; 502/512; 549/534
[58] Field of Search ............... 502/170, 243, 347, 348, 502/512

[56] References Cited

U.S. PATENT DOCUMENTS

| | | | |
|---|---|---|---|
| 1,878,962 | 9/1932 | Meidert | 106/310 |
| 3,578,690 | 5/1971 | Becker | 260/414 |
| 4,555,501 | 11/1985 | Armstrong | 502/243 |

FOREIGN PATENT DOCUMENTS 2043418A 10/1980 United Kingdom .

OTHER PUBLICATIONS

Encyclopeadia of Chemical Technology, 3rd Edition, vol. 3, pp. 372–373.

*Primary Examiner*—Patrick P. Garvin
*Attorney, Agent, or Firm*—Harold N. Wells

[57] ABSTRACT

A silver salt solution suitable for depositing silver on a support in the preparation of silver catalysts is made by reacting a silver compound with a neo-acid, in a hydrocarbon solvent. The reaction is completed under reflux conditions, thereby removing water formed by the reaction and reacting at least 90% of the unreacted acid. Therefore, the solution may be used without further processing to impregnate a porous support, thereby providing a catalyst useful for oxidation of ethylene oxide.

18 Claims, No Drawings

1

PROCESS FOR PREPARING SILVER CATALYSTS

PRIOR ART

The invention relates broadly to the preparation of solutions of silver salts and their use in the manufacture of silver catalysts. More particularly, the invention relates to a simplified procedure for preparing hydrocarbon solutions of silver salts of neo-acids which are useful for making ethylene oxide catalysts.

The effectiveness of silver catalysts made from solutions of silver salts of neo-acids was shown in U.S. Pat. No. 4,555,501 which is incorporated by reference into the present disclosure. The solutions were prepared by reacting a silver compound with a neo-acid and precipitating the silver salt. The crystals were separated, washed, and then dissolved in a solvent, thereby creating a concentrated silver salt solution which could be used to impregnate porous supports. This method, while producing pure silver salts which formed active and selective catalysts, is complex and therefore not well suited for commercial manufacture of such catalysts.

Metal salts of carboxylic acids are used for various purposes, such as in lubricants, antimicrobial agents, and driers, as discussed in U.S. Pat. No. 4,555,501. One method of making metallic salts involves the use of azeotroping agents to remove the water formed by reacting a metal compound with carboxylic acid, as mentioned in Kirk-Othmer, *Encyclopedia of Chemical Technology*, 3rd edition. Volume 3, pages 372-3. This is suggested also in U.S. Pat. No. 1,878,962. A similar technique was employed in U.S. Pat. No. 3,578,690 for preparing molybdenum and vanadium salts in organic solutions for use as homogeneous catalysts.

Direct preparation of silver salts in solution presents difficulties since, as disclosed in U.S. Pat. No. 4,555,501, the silver salts must be pure and may not contain significant amounts of free acid. However, it has now been found that such direct preparation of silver salt impregnating solutions is possible, as will be seen in the description which follows.

SUMMARY OF THE INVENTION

Supported silver catalysts may be prepared by impregnating a porous support with a solution comprising the silver salts of neo-acids, particularly silver neodecanoate. The invention relates to a one-step method of preparing such silver salts in solutions suitable for immediate use as an impregnating solution, i.e., without recovering the silver salt, and the use of such solutions in preparing supported silver catalysts for the oxidation of ethylene to ethylene oxide.

The method comprises mixing at least a stoichiometric amount of a silver compound for each unit amount of the neo-acid in sufficient solvent to dissolve the silver salt to be formed. The reaction is carried out at the boiling temperature of the mixture under the pressure selected, generally about 0.01 to 0.08 bar. Sufficient heat is provided to vaporize the water which is formed by the reaction and a portion of the solvent. The vapors are condensed and the insoluble water byproduct is phase-separated from the solvent and discarded, while the condensed solvent is returned to the reacting mixture. The reaction is continued until at least 90% of the neo-acid has been reacted, particularly, at least 95%, most preferably at least 98% of the neo-acid is reacted.

The solution may then be used to impregnate a porous support.

Useful silver compounds include, but are not necessarily limited to, silver oxide, silver carbonate, silver bicarbonate, and silver acetate. Silver oxide is preferred since it introduces nothing but silver and oxygen to the reacting mixture. The oxygen is removed as the water byproduct of the reaction.

The process is particularly useful for preparation of silver salts of neo-acids having 7 or more carbon atoms, particularly neodicanoic acid, since sufficient amounts of these acids can be dissolved so that impregnation of a porous support will produce a catalyst having a high silver content.

Preferably, slightly more than the stoichiometric amount of the silver compound is used so that the resulting solution contains an excess of silver, up to about 5% above that required to react with the acid.

The solvents are preferably hydrocarbons, particularly aromatics such as toluene, xylene, ethylbenzene, cumene, or pseudocumene. The solvent will be substantially immiscible with water so that byproduct water can be phase-separated from the condensed vapors. The solvents should be capable of dissolving large quantities of the silver salt in order to make it possible to place large amounts of silver on the porous support. Preferably, the weight ratio of silver salt to solvent will be above 1/1, up to 3.5/1.

The support may be impregnated in the silver salt solution by conventional tipping in an excess of solution, or preferably by contacting the support with about 70 to 130% of the amount of solution needed to fill the pores of the support. One particularly advantagous method is to use less solution than the support being impregnated can absorb, so that no excess of solution remains.

After impregnation, the inchoate catalyst is activated by heating, preferably in the presence of oxygen to decompose the silver salt, leaving a finely divided silver dispersion on the support. This may be done by heating in a batch oven to a maximum temperature of about 350° C., or, alternatively, by rapidly heating the impregnated support on a moving belt by passing air over it at a temperature of about 400° to 600° C.

The activated catalyst may be used directly without further treatment, but preferably an alkali metal, such as cesium, rubidium, or potassium, will be post-deposited.

DESCRIPTION OF THE PREFERRED EMBODIMENTS

As previously mentioned, the method of preparing silver salts of neo-acids disclosed in U.S. Pat. No. 4,555,501 was intended to separate pure crystals of the silver salt from the acid solution in which they were formed. After filtration, the crystals were washed to remove unreacted acid and water which remained in the reaction solution. Then the pure crystals were dissolved in a suitable hydrocarbon to prepare the impregnating solution. As demonstrated in Example 2 of the patent, a catalyst prepared using an incompletely reacted solution has inferior in performance compared to one prepared from pure crystals. We have now found that by properly carrying out the reaction it is possible to use the reacting solution as an impregnating medium in the preparation of supported silver catalysts and without separating the silver salt as a solid and redissolving it.

The reaction of a silver compound with a neo-acid is carried out under conditions which permit using the resulting solution at an impregnating medium for porous supports. By proper selection of the reactants and the reaction medium, and by operating under conditions set forth hereinafter, it has been found possible to provide a one-step preparation of an impregnating solution which provides catalysts equivalent to those prepared by dissolving pure crystals.

Whereas prior art methods generally employ water as a solvent, it is characteristic of the present invention, and the preparation of silver salts of neo-acids generally, that water is excluded from the solution. In the U.S. Pat. No. 4,555,501 it is taught that water should be limited to no more than 0.1 volume percent in the impregnating solution. Although it has been more recently found that the presence of water is not as detrimental as was previously believed, it may be removed during preparation of the impregnating solution according to the present invention as an indication of the extent to which the reaction forming the silver salt has proceeded. Since half a mol of water is formed when a mol of the neo-acid is reacted, substantial amounts of water may be removed from the reacting solution. It has been found that by proper selection of the solvent the water formed can be distilled off, then condensed and phase-separated from the solvent, which is returned to the reacting solution. The solvent should have the following characteristics:

it should be substantially insoluble in water;
it should have an atmospheric boiling point higher than the desired reaction temperature for the silver compound and the neo-acid and lower than the decomposition temperature of the silver salt;
it should dissolve large amounts of the silver salt to permit preparation of catalysts having a high silver content;
it should be easy to remove from an impregnated support; and
it should deposit silver as finely divided, evenly dispersed particles.

It has been found that hydrocarbons having 7 carbon atoms or more are most suitable, particularly aromatics such as toluene, xylene, cumene, pseudocumene, and the like. Of these, cumene is particularly useful. Organic compounds which could reduce the silver compound and form metallic silver prematurely are not considered desirable; therefore, oxygen-containing compounds, such as alcohols, glycols, ketones, ethers, etc., should be avoided. Inert liquids such as halogenated hydrocarbons could be used, but these are not preferred because of higher cost and/or difficulties in handling.

Various silver compounds could be used, which can react with the neo-acid to form the silver salt. Examples are silver oxide, silver carbonate, silver bicarbonate, and silver acetate. Preferably, silver oxide is used, since it introduces no undesirable anions to the solution and the water produced may be easily removed to complete the reaction.

Although the method may be used with carboxylic acids generally, it is particularly useful in preparation of silver salts of neo-acids, particularly neodecanoic acid. Neo-acids, sometimes called tri-alkyl acetic acids, are defined in U.S. Pat. No. 4,555,501 as being acids in which the carboxylic acid moiety is directly attached to three other carbon atoms, or to other carbon atoms which are so attached. Generally, neo-acids having 7 carbon atoms or more are preferred. Neo-decanoic acid is commercially available as a mixture of 67% 2-ethyl, 2-methyl heptanoic acid, 31% 2,2 dimethyl octanoic acid and 2% 2,2 diethyl hexanoic acid. The mixed neo-acids may be used as commercially available, or separated and the individual aids used for preparation of the silver salts.

Preparing an impregnating solution comprising the silver salt of a neo-acid in a solvent should be done in a closed apparatus in order that no solvent is lost. The silver compound, the acid, and the solvent may be introduced into a vessel in any order, but it is preferred that the solvent be added first to facilitate mixing. The amount of solvent is sufficient to dissolve the silver salt to be formed, providing a concentrated solution thereof. At least one half mol of silver compound will be added to each mol of acid, preferably a slight excess up to about 5% of the silver compound is used. As they are mixed, heat is released during the initial reaction. Thereafter, the mixture is heated to what is usually referred to as "reflux" conditions, that is, the boiling temperature of the mixture. Then, depending upon the amount of heat supplied, some of the liquids will be vaporized. This vapor is condensed and the liquid allowed to separate into immiscible water and solvent phases. The water phase is principally derived from the neutralization reaction; it is withdrawn and discarded; the solvent phase is returned to the reaction mixture. The reaction temperature will depend mainly upon the type and amount of solvent selected, the pressure in the apparatus, and the extent of the reaction. Generally, with pressures in the range of 0.01 to 0.08 bar, the temperature will be in the range of 70°–85° C. Since it is preferred to react at least 90 to nearly 100% of the acid, this factor, along with the reaction temperature, will determine the length of time required. Generally, this will require about 15 to 80 minutes, preferably about 20 to 60 minutes. When complete, the solution preferably will contain no more than about 0.2 weight percent free acid, and whatever excess of silver compound was chosen. The finished solution will be saturated with water. The concentration of the silver salt will depend upon the amount of solvent used, but where very concentrated solutions are wanted, the weight ratio of silver salt to solvent may be in the range of about 1/1 to 3.5/1. Fine adjustments can be made to the weight ratio by adding or removing solvent at this time.

Since silver catalysts prepared by the method of the invention are particularly useful in the oxidation of ethylene to ethylene oxide, the preferred support will be selected for such a use.

Preferred catalysts prepared in accordance with this invention contain up to about 15% by weight of silver, expressed as metal, deposited upon the surface and throughout the pores of a porous refractory support. Silver contents higher than 20% by weight of total catalyst are effective but result in catalysts which are unnecessarily expensive. Silver contents, expressed as metal, of about 5–13% based on weight of total catalyst are preferred, while silver contents of 7–12% are especially preferred.

Catalysts may be made with supports comprising alumina, silica, silica-alumina, or combinations thereof. Prefered supports are those containing principally alpha-alumina, particularly those containing up to about 15 weight percent silica. Especially preferred supports have a porosity of about 0.1–1.0 cc/gm and preferably about 0.2–0.5 cc/gm. Preferred supports also have a relatively low surface area, that is, about 0.2–1.5 m²/gm. Such surface-areas are determined by the BET method [J. Am. Chem. Soc. 60, 309–16 (1938)]. Porosities are determined by the mercury porosimeter method [see Drake and Ritter, "Ind. Eng, Chem, Anal. Ed." 17, 787 (1945)]. Pore diameters and pore diameter distributions are determined from the surface area measurements and the apparent porosity measurements.

For ethylene oxide catalysts, the preferred support will be capable of selectively adsorbing alkali metals, particularly potassium, rubidium, and cesium, from solutions of those metals. By this is meant the deposition of greater amounts of alkali metals than would be predicted by calculation from the amount and concentration of the solution absorbed by the support. The mechanism by which this is accomplished is not clear, but may involve ion exchange with other metal ions found on the support. In this regard it is of interest to note that published British patent application G.B. No. 2,043,418A teaches against the use of supports which contain ions exchangeable with the alkali metals (page 12, line 50). However, it has been found that the promotional effect of the alkali metals is enhanced when the support can selectively adsorb alkali metal ions. The present method of silver catalyst preparation includes steps which are intended to take advantage of this property of the preferred supports.

For use in commercial ethylene oxide production applications, the supports are desirably formed into regularly shaped pellets, spheres, rings, etc. Desirably, the support particles used have "equivalent diameters" in the range from 3–10 mm, and preferably in the range of 4–8 mm, which are usually compatible with the internal diameter of the tubes in which the catalyst is placed. "Equivalent diameter" is the diameter of a sphere having the same external surface (i.e., neglecting surface within the pores of the particle) to volume ratio as the support particles being employed.

The silver is added to the support by immersion of the support into a solution containing a silver salt of a neo-acid having 7 or more carbon atoms and being substantially free of water and said neo-acid. The silver-containing liquid penetrates by absorption and/or capillary action into the pores of the support. A single immersion or a series of immersions, with or without intermediate drying, may be used depending in part upon the concentration of the silver salt in the solution. To obtain catalysts having silver contents within the preferred range, suitable impregnating solutions will generally contain from 5–50 weight percent silver, expressed as metal, but supplied as silver salts of neo-acids. The exact concentration employed, of course, will depend upon, among other factors, the desired silver content, upon the nature of the support, the viscosity of the liquid, and the solubility of the neo-acid silver salt.

As indicated, the silver is deposited upon the support by immersion of the support into a solvent containing a silver salt of a neo-acid until the solution has been absorbed into the pores of the support. Typical immersion times of from 1 to 60 minutes at temperatures of from 30° to 120° C. will usually suffice to achieve silver contents of as high as 7–15 weight percent of silver.

In addition to the silver salts, the liquid in which the support is immersed may contain promoters, such as alkaline earth metal promoters, e.g., barium or alkali metals such as cesium, potassium and rubidium. Contrary to the usual silver solutions which contain water, it is characteristic of the present method to employ substantially water-free impregnating solutions, which will not readily dissolve the usual metal salts. However, it is feasible to prepare promoter metal salts of neo-acids which will be soluble in the solvent selected for use with the silver salts and thereby to introduce promoter metals into the silver impregnating solutions.

After a support has been impregnated with a solution of a silver salt of the selected neo-acid, the support is heated to decompose the salt, leaving activated silver. Subsequently, improved selectivity of oxidation of ethylene to ethylene oxide may be obtained by impregnating the activated silver catalyst with a solution of an alkali metal promoter, although this is not required.

The impregnating solution preferably contains the silver salt, e.g., silver neodecanoate, in a hydrocarbon solvent, such as toluene, ethylbenzene, xylene, cyclohexane, cumene, or pseudocumene. It is desirable that the solvent be capable of holding a large amount of the silver salt in order to permit preparation of silver catalysts having 7–15 weight precent silver in a single impregnation. Multiple impregnations can increase the silver content, but increase costs. However, the proportions of solvent and the silver salt may be adjusted as may be convenient for preparation of the catalyst. Typically, a weight ratio of silver salt/solvent of 1/1–3.5/1 may be used, particularly about 2/1. Depending upon the solvent, the silver salt, and the ratio of the two, the temperature of the impregnating solution may be at room temperature or above to provide the desired results.

Impregnation of the selected support may be achieved in conventional manner, that is, immersing the support in the silver salt solution described above for a period of time sufficient to saturate the pores of the support. The saturated support is removed from the solution and any excess drained off. An alternative and efficient method involves using slightly less solution than is required to fill the pores of the support, say, about 70 to 99.5%. This method has the advantage of using all of the solution prepared. After the support has been impregnated, it is activated by heating the impregnated particles to a sufficient temperature to remove the solvent and to decompose the silver salt, at least in part, to elemental silver.

Activation of the silver may be carried out by heating to temperatures of about 200° to 600° C., preferably 250° to 500° C., in the presence of air or reduced-oxygen atmospheres as desirable to control decomposition of the silver salts. The temperatures should be regulated so that the silver particles are highly active and suitable for oxidation of ethylene to ethylene oxide so that the catalyst can be used, even without the advantage obtained by post-deposition of an alkali metal(s). When the activation is carried out in a batch oven, the temperature will be raised gradually to a maximum of about 350° C. and held at the maximum temperature for a period of about one to two hours, until the silver particles have reached the desired size and all organic materials have been removed. In a one preferred procedure, the impregnated support is heated to about 100° C. over one hour, then to about 350° C. over two hours. Air will be passed over the silver-laden support during activation at a rate sufficient to assure oxygen is present at the surface of the support. Although air is the preferred gas, other gases may be used, but the presence of some oxygen is considered desirable. It is usual for the temperature to rise after decomposition of the silver salts has begun. This temperature excursion may be controlled by adjustment of the activation conditions.

Activation of the impregnated support distributed as a thin layer on a moving belt is particularly useful since by uniform activation of the catalyst appears to result. In this method air heated to about 400° to 600° C. is passed over the catalyst. The exposure of the impregnated support to the hot air may be quite brief, of the order of a minute or so. This method is particularly well suited to commercial production of large amounts of catalyst.

When used, the amount of alkali metal on the finished catalyst is generally similar to those employed heretofore. Thus, the amount deposited will be generally up to about $8 \times 10^{-3}$ gew/kg catalyst, preferably up to about $7 \times 10^{-3}$ gew/kg, and particularly about $1-6 \times 10^{-3}$ gew/kg (gew = gram equivalent weight) when relatively low surface area supports are used (i.e., up to about 1 m²/gm). However, it may be necessary to use greater amounts of alkali metal if supports having much larger surface areas are used. The alkali metals of the periodic table include sodium, lithium, potassium, rubidium, and cesium. For purposes of the present invention, the latter three alkali metals are particularly prefered, especially cesium, although sodium and lithium are not necessarily excluded. The alkali metal(s) will be supplied as metal compound(s) which may be associated with various anions, as, for example, hydroxides, nitrates, formates, and acetates. Conveniently, the alkali metal compounds may be dissolved in water or alcohol-water solutions, preferably ethanol:water solutions, containing only enough water to solubilize the alkali metal compound.

Catalysts prepared by the procedures described above have improved performance for use in the production of ethylene oxide by the vapor-phase oxidation of ethylene with molecular oxygen. Oxidation reaction conditions such as those previously known in the art may be employed. These usually involve reaction temperatures of about 150°–400° C., usually 200°–300° C., and reaction pressures in the range of from 0.5–20% ethylene and 3–15% oxygen, with the balance comprising comparatively inert materials including such substances as nitrogen, carbon dioxide, methane, ethane, argon, and the like. Small amounts of halogenated reaction modifiers, such as ethylene dichloride, may be used. Only a portion of the ethylene is reacted per pass over the catalyst; and after separation of the desired ethylene oxide product and the removal of appropriate purge streams and carbon dioxide to prevent uncontrolled build-up of inerts and/or byproducts, unreacted materials are returned to the oxidation reactor.

The following examples will illustrate the preparation and use of catalysts according to the invention and will support those aspects of the method previously disclosed as critical to achieving the desired results. Unless otherwise indicated, all parts and percentages are given by weight for liquids and solids, while for gases compositions are given as mol percent, and flow rates are given in normal cubic meters per hour, i.e., at 0° C. and 760 mm. Hg. The fraction of the reacted ethylene which is converted to ethylene oxide is given as the percent selectivity, as is usual in the art.

EXAMPLE 1

Into a 2000 cc flask are placed 431.5 gms of neo-decanoic acid (NDA) obtained from (Exxon Chemical Co.) and 350 gms of cumene. The flask is closed and connected to a Dean-Stark apparatus which will condense and separate water evolved from the flask during the formation of silver neo-decanoate. The liquid collecting portion is initially filled with additional cumene. The solution in the flask is heated to about 45° C., at which time 305.6 gms of silver oxide, $Ag_2O$, is slowly added over a period of about 20 minutes. A vacuum source is connected to reduce the pressure to about 20 mm Hg absolute (0.027 bar). The contents of the flask are heated slowly to bring the temperature to about 75° C., the reflux of the mixture once the excess water is removed. The vaporized cumene and water are condensed, and separated in the Dean-Stark apparatus. Two phases form, with the water phase being withdrawn and excess cumene returned to the flask. When 22.6 cc of water have been withdrawn the reaction is essentially complete and 32 gm of cumene is removed via reflux. Thereafter, the solution is filtered while hot and 18.0 gms of unreacted $Ag_2O$ is recovered, at which time the solution is ready for use as an impregnating solution. The solution contains 25.7 weight % silver and less than 0.17 weight % free acid.

EXAMPLE 2

A solution prepared in a similar manner to that described in Example 1 contained less than 0.172 weight % free neo-decanoic acid, as measured by titration with triethylamine of a solution in which the acid has been reacted with barium perchlorate to release perchloric acid. In order to demonstrate the importance of minimizing the free acid content, a series of catalysts were prepared in which free neodecanoic acid (NDA) was added to the impregnating solution. These catalysts are designated A-F in Table I below.

For each test a 210 gm sample of the support material ($\frac{1}{4}'' \times \frac{1}{4}''$ rings) is preheated to 85° C. and impregnated with 71 gms of the silver neo-decanoate:cumene solution at 80° C. for 30 minutes. The amount of solution used is predetermined as the amount which is about 5% less than the solution which the silver catalyst can absorb, leaving no residual solution to be drained. The saturated support is activated by placing it on a moving wire-mesh belt and passing the impregnated support through a zone where for about 1 minute it is exposed to an upward flowing stream of air having a temperature of 500° C. After cooling to room temperature, the catalyst is impregnated with a solution of cesium hydroxide in a water-ethanol mixture. This solution is prepared by dissolving cesium hydroxide in enough distilled water to make a solution containing 4 wt % of cesium. The 4 wt % solution is then mixed with anhydrous ethanol to produce a solution containing about 525 wt. ppm of cesium. The solution is circulated through the activated silver catalyst for 2 hours, after which time the excess solution is drained and then dried to produce a finished catalyst containing about 8.2 wt % silver and 220–440 weight ppm Cs by analysis. A charge of 36 gm of this catalyst was placed in a reactor consisting of $\frac{1}{4}''$ stainless steel ss tube which is heated in a salt-bath. A feed mixture of 7% $O_2$, 8% CO, 15% $C_2H_4$, 70% $N_2$, and 0.6 ppm ethylene dichloride was passed over the catalyst with a space velocity of 5500 $hr^{-1}$. The pressure was maintained at 21.69 bar and the temperature between 200°–300° C. as required to obtain an outlet concentration of 1.5 vol. % ethylene oxide (EO). The results of the tests are shown in the following table.

TABLE I

| Catalyst | Free NDA Added Wt. % | Ag. Wt % | Cs. Wt. PPM | Reactor temp °C. | % Selectivity to EO |
|---|---|---|---|---|---|
| A | None | 8.23 | 434 | 241 | 80.5 |
| B | 0.332 | 8.09 | 388 | 234 | 80.0 |
| C | 0.662 | 8.02 | 357 | 239 | 80.1 |
| D | 1.96 | 7.79 | 342 | 257 | 77.8 |
| E | 3.23 | 8.04 | 349 | 266 | 77.0 |
| F | 6.25 | 7.95 | 329 | 264 | * |

*Selectivity 77.5% at 1% EO at outlet. Not active enough to obtain 1.5% EO.

It is evident that the amount of free neo-decanoic acid remarkably affects the performance of the finished catalyst. Generally, therefore, the preparation of silver neodecanoate, or related silver neo-acid salts, should be carried to reduce the residual free acid to the greatest practicable extent, leaving no more than about 4 wt. % free acid. Preferably the free acid should be below 2 wt. % and most preferably below 1 wt. %. Expressed as a fraction of the inital neo-acid charged, the reaction to form the silver salt should be continued until at least 90% of the initial acid has been reacted, preferably at least 95%, and most preferably at least 98%.

EXAMPLE 3

Into a 2000 cc flask are placed 277 gms of neodecanoic acid (Exxon Chemical Co.) and 273 gms of psuedocumene. The flask is closed and connected to a Dean-Stark apparatus as in Example 1. An additional 27 gms of psuedocumene is placed in the Dean-Stark tube. The solution in the flask is heated to about 45° C. at which time 187 gms of silver oxide was added. A vacuum was gradually pulled on the flask and the flask heated to reflux conditions. Water was condensed and separated in the Dean-Stark apparatus until 14.5 cc had been removed and the vacuum reached about 30 minutes absolute (0.04 bar) with a flask temperature up 60° C. The reaction is essentially complete. The solution is filtered and 2.65 gms of $Ag_2O$ are recovered, representing a 98.6% conversion based on the initial $Ag_2$ charged. The solution is analyzed and found to contain 23.32 wt % silver and less than 0.17 wt. % free NDA. It is ready for use as an impregnating solution containing about 1.5 parts by weight of silver neodecanoate for each part of psuedocumene.

EXAMPLE 4

In a similar manner to that described in Example 1 and 3 a solution containing 2 parts by weight of silver neononanoate for each part of cumene is prepared. The apparatus is charged with 343 gms of neononanoic acid (Exxon Chemical Co.), 460 gms of cumene, and 257 gms of $Ag_2O$ as previously described. A vacuum is gradually pulled on the apparatus as the contents of the flask are refluxed until after about 3 hours 19.5 cc of water had been collected. The solution was filtered and 6.71 gms of $Ag_2O$ was recovered, indicating that about 97.4% of the initial $Ag_2O$ had been converted to silver neononanoate. The solution is concentrated by vaporizing cumene under vacuum until a solution having the desired concentration is obtained, which is analyzed to contain 27.65 wt. % silver and less than 0.17 wt. % free neononanoic acid. The solution is ready for use in impregnating a support.

What is claimed is:

1. A process for preparing catalysts suitable for oxidizing ethylene with molecular oxygen to ethylene oxide, comprising:
   (a) mixing at least a stoichiometric amount of a silver compound with a unit amount of a neo-acid having 7 or more carbon atoms in at least sufficient solvent to dissolve the silver salt to be formed;
   (b) reacting the mixture of (a) at the boiling temperature of said mixture under a pressure in the range of 0.01 to 0.08 bar for a period of time sufficient to react at least 90% of the neo-acid with said silver compound;
   (c) impregnating a porous support having a surface area of about 0.2 to $1.5 M^2/gm$ with the reacted mixture of (b); and
   (d) activating the impregnated support of (c) by heating for a period of time sufficient to produce an active ethylene oxide catalyst.

2. The process of claim 1 wherein said silver compound is silver oxide.

3. The process of claim 2 wherein the water or reaction is continuously removed.

4. The process of claim 2 wherein said silver oxide is present in up to 5% excess over the stoichiometric amount and said excess silver oxide is separated from the reacted mixture of (b) before the impregnation of (c).

5. The process of claim 1 wherein said neo-acid is neo-decanoic acid.

6. The process of claim 1 wherein said solvent is at least one member of the group consisting of toluene, xylene, ethylbenzene, pseudocumene, and cumene.

7. The process of claim 1 wherein the weight ratio of silver salt to solvent is in the range of 1/1 to 8. The process of claim 1 wherein the support is impregnated by immersion in an amount of the reacted solution of (b) in excess of the amount needed to fill the pores of the support.

9. The process of claim 1 wherein the support is impregnated by contact with an amount of the reaction solution of (b) less than the amount needed to fill the pores of the support.

10. The process of claim 9 wherein about 70 to 130% of the amount of reacted solution needed to fill the pores of the support is used.

11. The process of claim 1 wherein the impregnated support of (c) is activated in a batch oven by exposure to a temperature up to about 350° C.

12. The process of claim 1 wherein the impregnated support of (c) is activated on a moving belt by exposure to a stream of air at a temperature up to about 600° C.

13. The process of claim 1 wherein at least 95% of the neo-acid has reacted with the silver compound.

14. The process of claim 13 wherein at least 98% of the neo-acid has reacted with the silver compound.

15. The process of claim 1 wheren the reacted mixture of 16, contains no more than about 4 weight percent free neo-acid.

16. The process of claim 15 wherein the reacted mixture of (b) contains no more than about 2 weight percent free neo-acid.

17. The process of claim 16 wherein the reacted mixture of (b) contains no more than about 1 weight percent free of neo-acid.

18. The process of claim 1 further comprising the step of:
   (e) post-impregnating the activated catalyst of
   (d) with a solution of an alkali metal compound.

* * * * *